(12) United States Patent
Hatcher et al.

(10) Patent No.: US 8,778,035 B2
(45) Date of Patent: Jul. 15, 2014

(54) PROCESS FOR THE SELECTIVE PRODUCTION OF HYDROCARBON BASED FUELS FROM ALGAE UTILIZING WATER AT SUBCRITICAL CONDITIONS

(75) Inventors: Patrick G. Hatcher, Suffolk, VA (US); Elodie Salmon, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 424 days.

(21) Appl. No.: 13/096,016

(22) Filed: Apr. 28, 2011

(65) Prior Publication Data

US 2011/0314881 A1 Dec. 29, 2011

Related U.S. Application Data

(60) Provisional application No. 61/358,207, filed on Jun. 24, 2010, provisional application No. 61/470,853, filed on Apr. 1, 2011.

(51) Int. Cl.
*C10L 1/18* (2006.01)
*C12P 5/00* (2006.01)
*C12N 1/12* (2006.01)

(52) U.S. Cl.
USPC ............ 44/605; 44/308; 435/166; 435/257.1

(58) Field of Classification Search
USPC ................................ 44/605; 435/166, 257.1
See application file for complete search history.

(56) References Cited

U.S. PATENT DOCUMENTS

| | | | |
|---|---|---|---|
| 2006/0099693 A1 | 5/2006 | Kobzeff et al. | |
| 2007/0006523 A1 | 1/2007 | Myllyoja et al. | |
| 2009/0077863 A1 | 3/2009 | Oyler | |
| 2009/0283442 A1 | 11/2009 | McCall et al. | |
| 2010/0050502 A1* | 3/2010 | Wu et al. .................. | 44/308 |
| 2011/0196132 A1 | 8/2011 | Kale | |
| 2011/0245444 A1 | 10/2011 | Miller et al. | |
| 2011/0314881 A1 | 12/2011 | Hatcher et al. | |

FOREIGN PATENT DOCUMENTS

| WO | 2009039333 A1 | 3/2009 |
|---|---|---|
| WO | 2010021753 A1 | 2/2010 |
| WO | 2010030196 A1 | 3/2010 |

OTHER PUBLICATIONS

Metzger et al., *Botryococcus braunii*: a rich source for hydrocarbons and related ether lipids. Applied Microbiology and Biotechnology, vol. 66 (2005) pp. 486-496.*

Radakovits et al., Genetic engineering of algae for enhanced biofuel production. Eukaryotic Cell, vol. 9, No. 4 (Feb. 5, 2010) pp. 486-501.*
Berkaloff et al., The resistant polymer of the walls of the hydrocarbon-rich alga *Botryococcus braunii*. Phytochemistry, vol. 22, No. 2 (1983) pp. 389-397.*
Allard et al., An improved method for the isolation of artifact-free algaenans from microalgae. Organic Geochemistry, Vil. 28, No. 9/10 (1998) pp. 543-548.*
Notification of Transmittal, International Search Report and Written Opinion of the International Searching Authority dated Feb. 9, 2012, from the corresponding International Application No. PCT/US2011/041039 filed Jun. 20, 2011.
Energy & Fuels 2004, 18, 590-598, Overview of Applications of Biomass Fast Pyrolysis Oil, S. Czernik and A. V.Bridgwater, National Bioenergy Center NREL, Golden, Colorado, and Bio-Energy Research Group, Aston University, Birmingham, UK. Received Oct. 1, 2003. Revised Manuscript Received Jan. 19, 2004.
Effects of Diagenesis and Catagenesis on Ladderane Lipids as Determined by Hydrous Pyrolysis, Andrea Jaeschke, Michael D. Lewan, Stefan Schouten and Jaap S. Sinninghe Damste, 1) Royal Netherlands Institute for Sea Research, Dep. Marine Biogeochemistry & Toxicology, Texel, The Netherlands, 2) US Geological Survey, Denver, Colorado (2 pages).
Effects of diagenesis and catagenesis on ladderane lipids as determined by hydrous pyrolysis, Andrea Jaeschke, Michael D. Lewan, Stefan Schouten, Jaap S. Sinninghe Damste, 1) NIOZ Royal Netherlands Institute for Sea Research, Dep. Marine Biogeochemistry & Toxicology, The Netherlands, 2) US Geological Survey, Denver, Colorado (Poster).
Chapter 13, Chitin: 'Forgotten' Source of Nitrogen, From Modern Chitin to Thermally Mature Kerogen: Lessons from Nitrogen Isotope Ratios, A. Schimmelmann, R. P. Wintsch, M. D. Lewan, and M. J. DeNiro, 1) Dept. of Geological Sciences, Indiana University, Bloomington, IN, 2) US Geological Survey, Lakewood, Co, 3) Dept. of Geological Sciences, University of California, Santa Barbara, CA, 1998 American Chemical Society, pp. 226-242
Organic Geochemistry 40 (2009) 416-427, Thermal decomposition process in algaenan of *Botryococcus braunii* race L. Part 2: Molecular dynamics simulations using the ReaxFF reactive force field, Elodie Salmon, Adri C.T. van Duin, Francois Lorant, Paul-Marie Marquaire, William A. Goddard III, 2008 Elsevier Ltd.

(Continued)

*Primary Examiner* — Jon P Weber
*Assistant Examiner* — Kara Johnson
(74) *Attorney, Agent, or Firm* — Young Basile

(57) ABSTRACT

Disclosed herein is the production of hydrocarbon based fuel from micro-organisms and algae that comprise algaenan without requiring prior removal of water, as well as the production of hydrocarbon based fuel directly from the algaenan itself. Also disclosed herein are feed material for the processes disclosed herein comprising modified algae and algaenan that selectively produce hydrocarbon of desired chain lengths, along with the process of modifying the algae and algaenan. Also disclosed herein is the production of both hydrocarbon and organic fertilizer from algae without the need to remove the water from the algae prior to processing.

18 Claims, 6 Drawing Sheets

(56) References Cited

OTHER PUBLICATIONS

Kumar, 'Microalgae to biofuels using sub- and supercritical water technology'; Presented at Energy Technology Partnership Forum, Williamsburg, VA, US (Apr. 13, 2011); see pp. 7, 10-14, 18, 21 and 22.

Notification of Transmittal, the International Search Report and the Written Opinion of the International Searching Authority dated Mar. 22, 2013, from the corresponding International Patent Application No. PCT/US2012/068420 filed Dec. 7, 2012.

Effects of Diagenesis and Catagenesis on Ladderane Lipids as Determined by Hydrous Pyrolysis, Andrea Jaeschke, Michael D. Lewan, Stefan Schouten and Jaap S. Sinninghe Damste, 1) Royal Netherlands Institute for Sea Research, Dep. Marine Biogeochemistry & Toxicology, Texel, The Netherlands, 2) US Geological Survey, Denver, Colorado (2 pages), 2005.

Effects of diagenesis and catagenesis on ladderane lipids as determined by hydrous pyrolysis, Andrea Jaeschke, Michael D. Lewan, Stefan Schouten, Jaap S. Sinninghe Damste, 1) NIOZ Royal Netherlands Institute for Sea Research, Dep. Marine Biogeochemistry & Toxicology, The Netherlands, 2) US Geological Survey, Denver, Colorado (Poster), 2005.

Pergamon, Organic Geochemistry 30 (1999) 1495-1507, Similarities and differences in hydrous pyrolysis of biomass and source rocks, Tanja Barth, Department of Chemistry, University of Bergen, Bergen, Norway.

Energy & Fuels 2004, 18, 590-598, Overview of Applications of Biomass Fast Pyrolysis Oil, S. Czernik and A. V. Bridgwater, National Bioenergy Center NREL, Golden, Colorado, and Bio-Energy Research Group, Aston University, Birmingham, UK, Received Oct. 1, 2003. Revised Manuscript Received Jan. 19, 2004.

Energy & Fuels 2007, 21, 1792-1815, Historical Developments in Hydroprocessing Bio-oils, Douglas C. Elliott, Pacific Northwest National Laboratory, Richland, Washington, Received Jan. 25, 2007, Revised Manuscript Received Mar. 16, 2007.

Pergamon, Geochimica et Cosmochimica Acta, vol. 61, No. 17, pp. 3691-3723, 1997, Elsevier Science Ltd., Experiments on the role of water in petroleum formation, M.D. Lewan, US Geological Survey, Denver, Colorado, Received Apr. 23, 1996, accepted in revised form Apr. 25, 1977.

Organic Geochemistry 39 (2008) 1735-1741, Thermal stability of ladderane lipids as determined by hydrous pyrolysis, Andrea Jaeschke, Michael D. Lewan, Ellen C. Hopmans, Stefan Schouten, Jaap S. Sinninghe Damste, a) NIOZ Royal Netherlands Institute for Sea Research, Department of Marine Organic Biogeochemistry, Texel, The Netherlands, b) US Geological Survey, Denver, Colorado.

Energy & Fuels 2006, 20, 848-889, Pyrolysis of Wood/Biomass for Bio-oil: A Critical Review, Dinesh Mohan, Charles U. Pittman, Jr., and Philip H. Steele, Dept. of Chemistry, Mississippi State University, Mississippi State, Mississippi, Environmental Chemistry Division, Industrial Toxicology Research Centre, Lucknow, India, and Forest Products Dept., Mississippi State University, Mississippi State, Mississippi, Received Jul. 28, 2005, Revised Manuscript Received Dec. 15, 2005.

Chapter 13, Chitin: 'Forgotten' Source of Nitrogen, From Modern Chitin to Thermally Mature Kerogen: Lessons from Nitrogen Isotope Ratios, A. Schimmelmann, R. P. Wintsch, M. D. Lewan, and M. J. DeNiro, 1) Dept. of Geological Sciences, Indiana University, Bloomington, IN, 2) US Geological Survey, Lakewood, Co, 3) Dept. of Geological Sciences, University of California, Santa Barbara, CA, 1998 American Chemical Society, pp. 226-242.

Energy & Fuels 1999, 13, 914-921, Fuel Oil Quality of Biomass Pyrolysis Oils—State of the Art for the End Users, Anja Oasmaa and Stefan Czernik, VTT Energy, Espoo, Finland, and NREL, Golden, Colorado, Received Dec. 22, 1998, Revised Manuscript Received Mar. 18, 1999, 1999 American Chemical Society.

Organic Geochemistry 40 (2009) 400-415, Thermal decomposition processes in algaenan of *Botryococcus braunii* race L. Part 1: Experimental data and structural evolution, Elodie Salmon, Francoise Behar, Francois Lorant, Patrick G. Hatcher, Pierre Metzger, Paul-Marie Marquaire, 2008 Elsevier Ltd.

Extended European Search Report completed on Dec. 13, 2013, from the corresponding EP Application No. 11798697.6.

\* cited by examiner

US 8,778,035 B2

PROCESS FOR THE SELECTIVE PRODUCTION OF HYDROCARBON BASED FUELS FROM ALGAE UTILIZING WATER AT SUBCRITICAL CONDITIONS

CROSS REFERENCE TO RELATED APPLICATIONS

This application claims priority to U.S. Provisional Application Ser. No. 61/358,207 filed on Jun. 24, 2010 and to U.S. Provisional Application Ser. No. 61/470,853 filed on Apr. 1, 2011, both incorporated herein in their entirety.

FIELD OF THE INVENTION

The present invention relates in general to the production of hydrocarbon-based fuel from both algae biomass and aliphatic biopolymers of algae.

BACKGROUND

The recent emphasis on finding alternative energy sources to fuel the energy needs of the United States and the world is leading to an accelerated search for new sources of fuel. Producing fuel from biomass is an important focus of many alternative energy strategies. Refined vegetable oils have been the typical starting materials for the production of biodiesel. Interest in algae as a possible source of fuel has soared in recent years because of associated advantages that include, but not limited to, (1) removing $CO_2$ from the atmosphere (2) non competition with agricultural crops and (3) potential for greater gallon per acre biofuel production than currently used crops.

Current processes for the production of biofuel from algae biomass and other microorganisms primarily involves the conversion of triglycerides within algal biomass to either fatty acid methyl esters by trans-esterification or to hydrocarbon-based fuels by various catalytic high-temperature processes which convert the algal oils to hydrocarbon-based fuels. Most of the focus has been on the triglycerides present within the lumens of the cells and the phospholipids that constitute the membrane lipids. However, one of the issues with current processes is the removal of algae out of the water, and the water out of the algae.

SUMMARY

Disclosed herein is the production of hydrocarbon based fuel from micro-organisms and algae that comprise algaenan without requiring prior removal of water, as well as the production of hydrocarbon based fuel directly from the algaenan itself. Also disclosed herein are feed material for the processes disclosed herein comprising modified algae and algaenan that selectively produce hydrocarbon of desired chain lengths, along with the process of modifying the algae and algaenan. Also disclosed herein is the production of both hydrocarbon and organic fertilizer from algae without the need to remove the water from the algae prior to processing.

One process disclosed herein for producing selective hydrocarbons from algae comprises providing a feed material of water saturated algae, subjecting the water saturated algae to water at a subcritical temperature for a predetermined period of time in a reactor, collecting a liquid product from the reactor and separating the hydrocarbons from the aqueous liquid phase product.

Another process disclosed herein for producing selective hydrocarbons from algae comprises extracting algaenan from algae, subjecting the algaenan to water at a subcritical temperature for a predetermined period of time in a reactor, collecting a liquid product from the reactor and separating the hydrocarbons from the aqueous liquid phase product.

Another process disclosed herein for producing hydrocarbons and organic fertilizer from one feed material comprises subjecting the water saturated algae having algaenan to water at a subcritical temperature for a predetermined period of time in a reactor, collecting a liquid product from the reactor, separating the hydrocarbons from the aqueous liquid phase product and collecting a liquid remaining after separating the hydrocarbons from the aqueous liquid phase product as organic fertilizer.

Also disclosed herein is feed material for use in producing select hydrocarbons comprising genetically modified algae having algaenan, as well as a feed material for use in producing select hydrocarbons comprising algaenan extracted from algae and subsequently chemically modified.

BRIEF DESCRIPTION OF THE DRAWINGS

The description herein makes reference to the accompanying drawings wherein like reference numerals refer to like parts throughout the several views, and wherein:

(FIG. 1A), of the biomass treated by acid hydrolysis (FIG. 1B) or with sodium hydroxide (FIG. 1C). Regions L correspond to lipidic structures from the algaenan, C to carbohydrate and P to proteins.

DETAILED DESCRIPTION

Figure 1A:
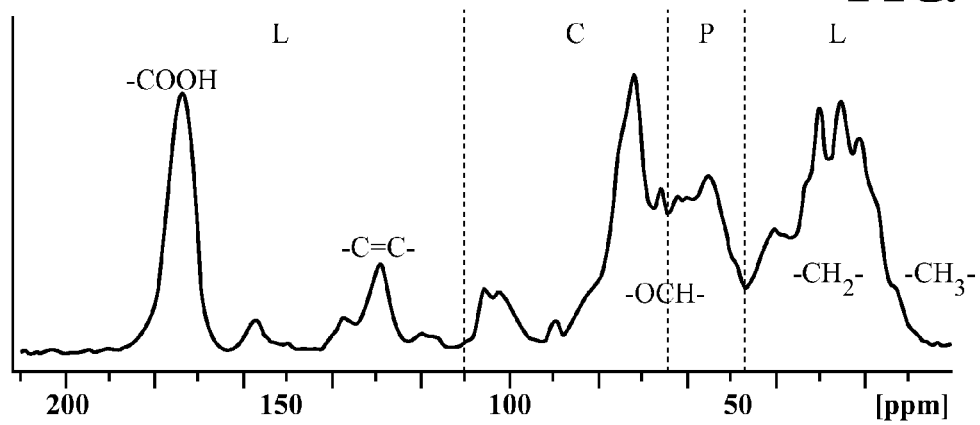
FIGS. 1A-1C are $^{13}C$ cross polarization magic angle spinning nuclear magnetic resonance (CPMAS NMR) spectra of freeze dried *Scenedesmus* sp.

Some species of green algae and other micro-organisms such as *Botryococcus braunii*, *Scenedesmus* sp., various dinoflagellates, and various eustigmatophytes, are able to metabolize single- or multi-layer protective outer walls that are composed of an aliphatic biopolymer called algaenan. This protective algaenan biopolymer is a recalcitrant material that is insoluble and non-hydrolyzable. It persists in sediments and is thought to be converted into petroleum over geological time. Disclosed herein are processes for producing hydrocarbon based fuel from these algaes without removing water, as well as producing hydrocarbon based fuel from the algaenan biopolymer contained within the algae or isolated from algae. As used herein, "water saturated algae" is algae and microorganisms taken directly from the water and processed without the total removal of the water. In the specification, "water saturated algae" is referred to as algae. The chain lengths of the hydrocarbon product range primarily between $C_{10}$ and $C_{30+}$, which is equivalent to a crude oil fraction that can be refined by a traditional refinery to kerosene ($C_{10}$-$C_{15}$), diesel fuel ($C_{16}$-$C_{18}$), and lubricating oil ($C_{19+}$).

Processes and feed materials are disclosed that have a cracking mechanism that yields algae-crude, which has similar properties to paraffinic petroleum but will not have the deleterious aspects of fossil fuels such as sulfur and aromatic components, which contribute disproportionately to environmental pollution. The process employs reproducing the natural process of thermal cracking and expulsion that takes place, for example, in buried shales to produce petroleum. The production of a hydrocarbon-based crude oil from algae will enable a domestic, commercial, alternative, carbon-neutral, feedstock for existing refineries. The disclosed processes provide a high-value algae-crude product from algae without the removal of water that supplements the conventional methyl ester biofuel product being exploited commercially and automatically enhances the yield of biofuels from this biomass source. The feed materials disclosed herein provide a feedstock that can be readily and directly converted to a refinable hydrocarbon fuel. Also disclosed is varieties of algae-crude that can be produced from different algal species, relating chemical composition of the algae-crude to algaenan structures via a mechanistic scheme.

The processes disclosed herein produce hydrocarbon based fuel from micro-organisms and microalgae (referred together herein as "algae") that comprise the biopolymers or algaenan (both referred to herein as "algaenan"), as well as producing hydrocarbon based fuel directly from the algaenan itself.

Algae, prevalent in both fresh and marine waters, are remarkable and efficient biological factories capable of producing substantially more biofuel than most typical land plants. Some forms of algae have a lipid content of up to 50% or more of their dry weight, and much of the biomass is convertible to biodiesel. Algal culturing requires significantly less land than other plant feed stocks, which can affect agricultural production. Some microalgae are capable of producing about thirty times the amount of oil per unit area of land, compared to terrestrial crops. Microalgae can exhibit doubling rates of once or twice a day, making them among the most efficient organisms at converting sunlight and atmospheric $CO_2$ into biomass. They can grow photosynthetically so that no carbon source other than $CO_2$ is required for growth. The combustion of any fuel from this biomass source will yield $CO_2$ previously fixed from existing atmospheric $CO_2$ so that the energy supply will be regarded as $CO_2$ neutral.

The algae-crude product can be produced directly from the algae disclosed herein, that is algae comprising the algaenan without removing water, referred to herein as feed material. The use of algae directly as feed material eliminates the need to extract the algaenan prior to processing. However, algaenan can also be isolated from the algae prior to processing and used as the feed material. Using the whole algae provides a useful co-product from the proteins and carbohydrates, whereas using algaenan will reduce the production of a useful co-product as it has less proteins and carbohydrates because these have already been removed by the algaenan isolation process prior to pyrolysis.

Algaenan is most abundant and diverse in green algae from the genera *Scenedesmus, Tetraedron, Chlorella, Botryococcus* and *Haematococcus*. Numerous chemical procedures have been proposed for the isolation of algaenan from algae. They typically consist of treatment with a succession of organic solvents, acids, and bases, all of which lead to the removal of free lipids, carbohydrates and proteins. However, these processes are cost prohibitive and labor intensive. For example, a concentrated algae paste comprised mainly of *Scenedesmus* sp. and 80 weight percent water can be used. The algae can be collected at an open pond algae farm. The algae and water mixture, or water saturated algae, can be treated with a 6N hydrochloric acid (HCl) solution under reflux for 18 hours or with a 0.5N sodium hydroxide (NaOH) solution at 60° C. for 4 hours. The methods are not limited to the use of HCl or NaOH. The use of other acids and bases or physical and other chemical methods is contemplated.

Figure 1B:
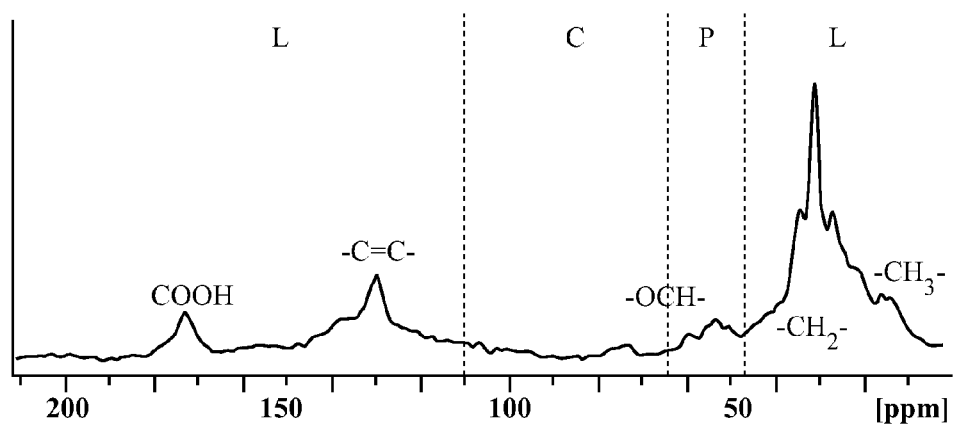
Figure 1C:
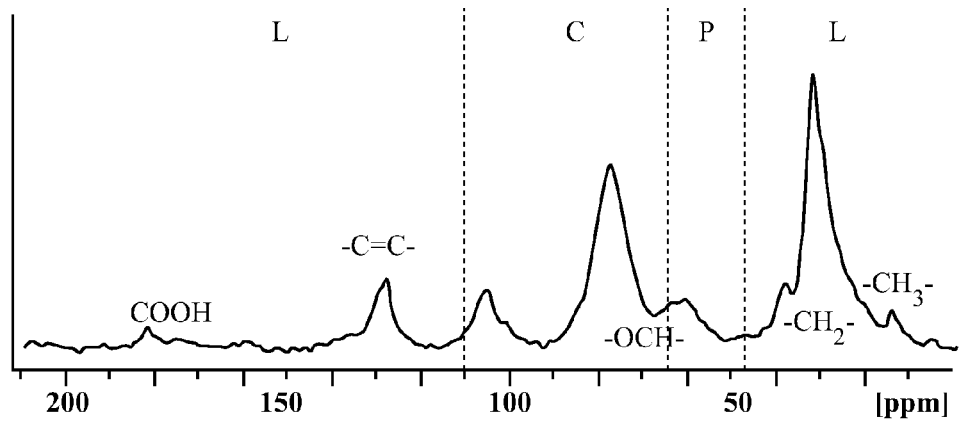

The initial algae sample and the biopolymer collected at the end of both treatments have been analyzed by $^{13}C$ cross polarization magic angle spinning nuclear magnetic resonance ($^{13}C$ CPMAS NMR, spectra in FIGS. 1A-C). In the spectra, lipid structures correspond essentially to peaks within the two regions L, carbohydrates are peaks within region C and proteins are peaks in region P and part of the peak ascribed to carboxylic groups (—COOH) in region L. Spectrum 1 of FIG. 1A is of freeze dried *Scenedesmus* sp., spectrum 2 of FIG. 1B is of the algaenan material resulting from the acid hydrolysis, and spectrum 3 of FIG. 1C is of the algaenan material resulting from basic treatment. From FIGS. 1A-C, it can be seen that enriched algaenan isolated after the acid hydrolysis (FIG. 1B) is comprised mainly of lipids. Almost all of the carbohydrates and proteins are removed. The enriched algaenan material isolated under basic treatment (FIG. 1C) still contains significant carbohydrates and proteins, but the algaenan material is more concentrated in lipid structures than the algae. Use of a stronger base, e.g., 5M NaOH, can be more effective in removing carbohydrates and proteins.

As noted, different varieties of algae-crude can be produced from different algal species, with the chemical composition of the algae-crude related to algaenan structures via a mechanistic scheme. This direct relationship between key structures in the algaenan and the specific hydrocarbon distributions generated by the processes herein can dictate the position and quantity of these key structures. This structural product/precursor link impacts the quality of algae-crude produced from algae and can be directed specifically for the production of gasoline, diesel and/or jet fuel. Without being bound to any specific theory, it is believed that one of the key aspects for converting algaenan to hydrocarbons is the nature and position of the different oxygen functional groups and the double bond positions.

Structural identification of the algaenan has been widely delineated by use of both invasive and non-invasive techniques. These analyses show that the algaenan is predominantly composed of highly aliphatic structures, linear or branched, connected to ester, acetal, and/or aldehyde groups. Depending upon the algal species, algaenan's structure may be more or less cross-linked by ether bridges but also by ester and acetal functional groups. In studies by Salmon et al. (see 2009a and 2009b, defined below), incorporated herein by reference, the initial steps involved with the thermal decomposition of the algaenan were described by combining experimental observations with numerical molecular model computations. See Salmon, Elodie; Behar, Francoise; Lorant, Francois; Hatcher, Patrick G.; Metzger, Pierre; Marquaire, Paul-Marie, 2009a; Thermal decomposition processes in algaenan of *Botryococcus braunii* race L. Part 1: Experimental data and structural evolution; Organic Geochemistry, 40(3), 400-415 and Salmon, E.; van Duin, A. C T.; Lorant, F.;

Marquaire, P-M.; Goddard III, W. A.; 2009b; Thermal decomposition process in algaenan of *Botryococcus braunii* race L; Part 2: Molecular dynamics simulations using the ReaxFF reactive force field; Organic Geochemistry, 40 (3), 416-427.

Figure 2:
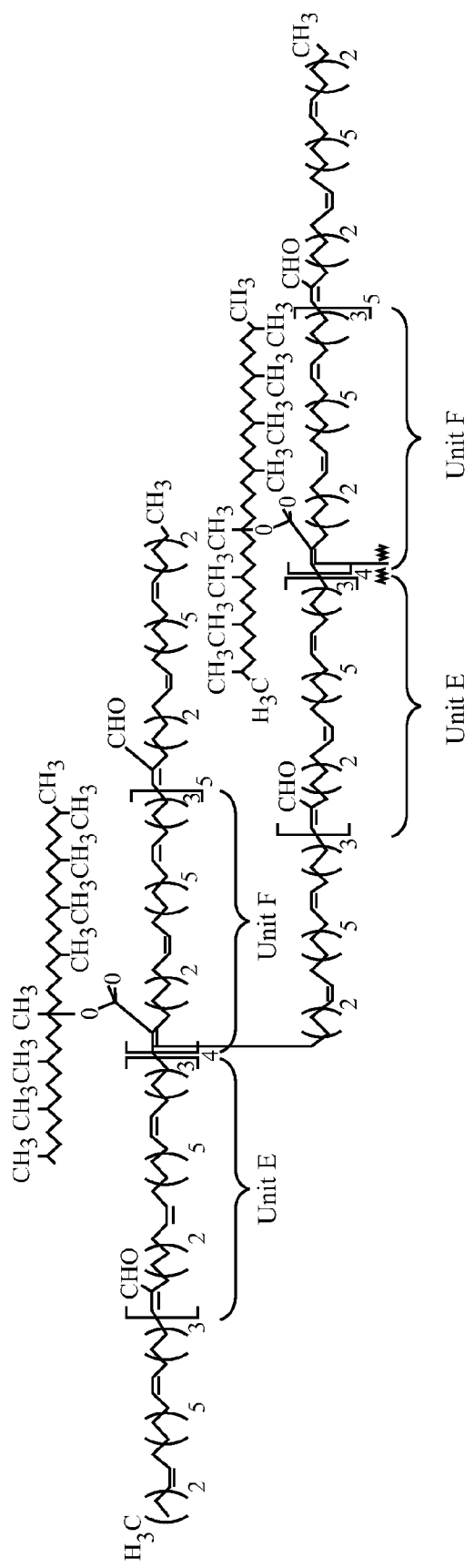
FIG. 2 is a revised algaenan structural model for *Botryococcus braunii* race L using 2D NMR data.

The cracking experiments performed all suggest that the main thermal degradation involves cleavage of esters and aldehydes, and cracking of the C—C backbone. The numerical molecular modeling simulations confirm the experimental observations and show that the weakest bonds in this algaenan structure correspond to the C—O and C—C bonds of the ester and the C—C bonds adjacent to the double bonds whereas the aldehyde groups remain stable during the numerically simulated thermal decomposition. The distribution of compound series produced essentially depends on the nature and the position of the functional groups in the alkyl structure and the homolytic cleavage adjacent to the carboxylic group is a dominant process in the cracking of functionalized alkyl structures. FIG. 2 below is a structural model for *Botryococcus braunii* race L.

Figure 3A:
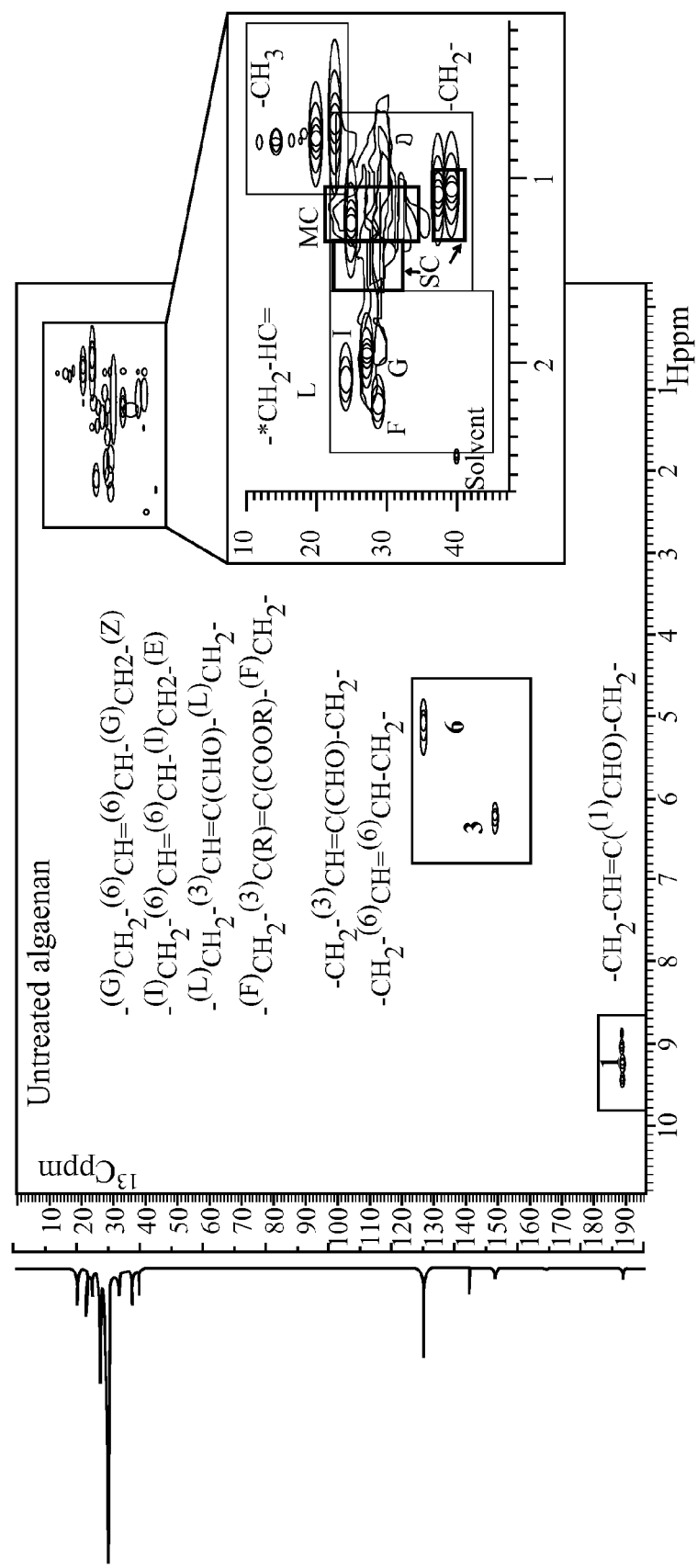
FIGS. 3A and 3B are each a two dimensional NMR spectra of the initial algaenan from *B. braunii* race L (FIG. 3A) and its residue (FIG. 3B) obtained at 300° C. in closed pyrolysis. Cross peaks in the MC boxes correspond to linear aliphatic structures and SC boxes correspond to branched aliphatic chains.
Figure 3B:
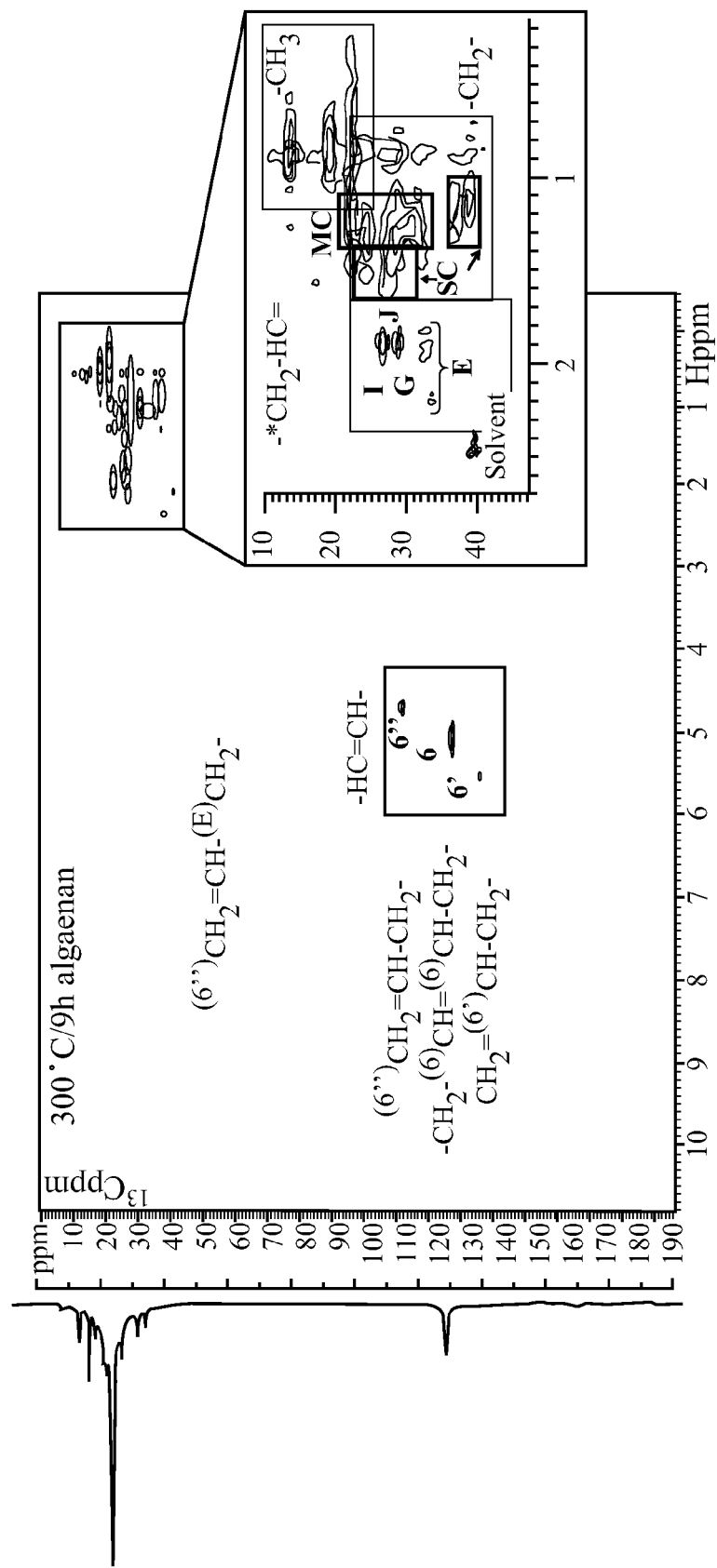

FIGS. 3A and 3B illustrate the different E and Z double bond conformation (respectively, peaks I and G), and the differentiation between mid-chain (peaks 3 and 6) and terminal olefins (peaks 6' and 6"). Also for oxygenated groups, different cross peaks can be specifically assigned to alcohol and ether groups and different chemical shifts also are observed for the methylene groups in a positions to an aldehyde, ester, or carboxylic groups that are in mid-chain or terminal positions. The larger molecular weight building blocks of the algaenan macromolecular structure can be correlated to the hydrocarbons produced from the particular algae.

The hydrocarbon distribution produced from the algaenan can be "tuned", or modified, by incorporating additional key elements to the native algaenan. One way to achieve this is by treating the algaenan with sodium hydroxide, which involves a saponification of the ester functions and leads to the formation of sodium salts of fatty acids. Without being bound to any specific theory, we believe that the sodium salt acts like an anchor on the carboxylic acid groups of the fatty acid, the same way that the ester functions are immobilized in the algaenan structure leading to facile cleavage of the carboxylic group (acid or ester) under pyrolytic conditions. Formation of a sodiated fatty acid greatly influences the distribution of hydrocarbons produced by pyrolysis and the nature of the hydrocarbon products from pyrolysis of solid algaenan can be altered in a way that makes them more valuable as fuel constituents. As a non-limiting example, algaenan samples are treated with dilute (0.5 M) aqueous sodium hydroxide solution to deprotonate fatty acid groups associated with the structure and produce sodium salts.

Another tuning approach is oxidative polymerization of the algaenan. This reaction is a well known process that is, for example, responsible for the drying of linseed oil-based paints and consists of sunlight-mediated autoxidation reaction of triacylglycerols containing unsaturated fatty acids. Oxygen groups are added to the double bonds of the algaenan and the degree of crosslinking is increased in the biopolymer structure. By increasing the number of oxygen groups the number of potential cracking sites is increased. Oxidative polymerization is directly related to the chemical reactivity of unsaturated fatty acids that compose the oils. First a process of autoxidation, which involves the oxidation of the double bonds by the oxygen in air, is occurring and resulting in the formation of peroxides. Second a polymerization takes place by the formation of peroxide radicals, resulting in an increased amount of cross-linking between the unsaturated acid molecules. As unsaturated acids and esters are the main components of the algaenan structure, the number of oxygenated functional groups and cross-linking structures can be increased by way of oxidative polymerization.

This polymerization strategy modifies the algaenan structure through its cross-link density, affecting the pyrolysis product distributions of hydrocarbons. A more highly cross-linked algaenan may produce smaller-chain hydrocarbon fragments because the number of anchor points between the linear chains would be smaller. The result would be a process in which one can "tune" the algaenan polymer to the production of desired fuels.

A third way to incorporate key elements into the structure of the algaenan is by genetically modifying the algae itself and growing cultures of algae specialized in the production of algaenan that is tuned for the production gasoline, diesel and/or jet fuel. Creation of designer algaenan alga to produce improved algaenan material that can be more readily processed to "drop-in-ready" liquid transportation fuel is contemplated. This could be done by introducing novel cracking points into the algaenan structure through genetic molecular engineering of its biosynthesis pathway of the genes responsible for algaenan formation. The growth conditions impact the production of the algaenan, as well as the relationship between lipids and algaenan production by different algae species.

Without being bound to a specific theory, it is expected that the formation of algaenan may serve as a hydrocarbon storage sink and/or provide a resistant cell-wall material against certain environmental stress and/or microbial attack. Therefore, the environmental stress factors such as high actinic light intensity, hot and cold temperature, elevated oxygen concentration (oxidative stress), high and low pH, and salinity may have an impact. Factors that are known to potentially favor or inhibit the synthesis of hydrocarbons, such as the lower availability of nitrogen nutrient or the addition of SC5058 (a cinnolinyl acid derivative [1-N-benzyl-3-carboxy-4-keto cinnoline]) in the growth medium may also have an impact. The rationale for this is that synthesis of hydrocarbons or fatty acids is likely related to algaenan biosynthesis through cross linking or polymerization of hydrocarbon backbones.

Average algal biomass used herein is composed of approximately 50% protein, 20% carbohydrates, 10% refractory biopolymer (algaenan), and 15% lipid. The feed material may be used directly from the process after harvesting. However, the feed material can also be freeze-dried if desired. As water is heated in the subcritical temperature range (i.e., below 374° C.), its properties change; hydrogen bonding decreases between water molecules as the temperature increases which in turn causes its dissociation constant to increase (i.e. increase in hydroxide and hydronium ion concentration). This increase in the hydroxide and hydronium ion concentration enable water to become a hydrolyzing reagent capable of hydrolyzing/depolymerizing the lipids, carbohydrates, and proteins; thus effectively isolating the algaenan. Since the algaenan is non hydrolyzable, it undergoes pyrolytic cracking and oil is produced. This process occurs whether the algaenan is a pure isolate or it exists as it does in whole algae, mixed with carbohydrates, proteins, and lipid triglycerides.

One process for subjecting the feed material to the subcritical temperature range is hydrous pyrolysis. Examples of producing algae-crude from the feed materials disclosed herein are provided below.

Figure 4:
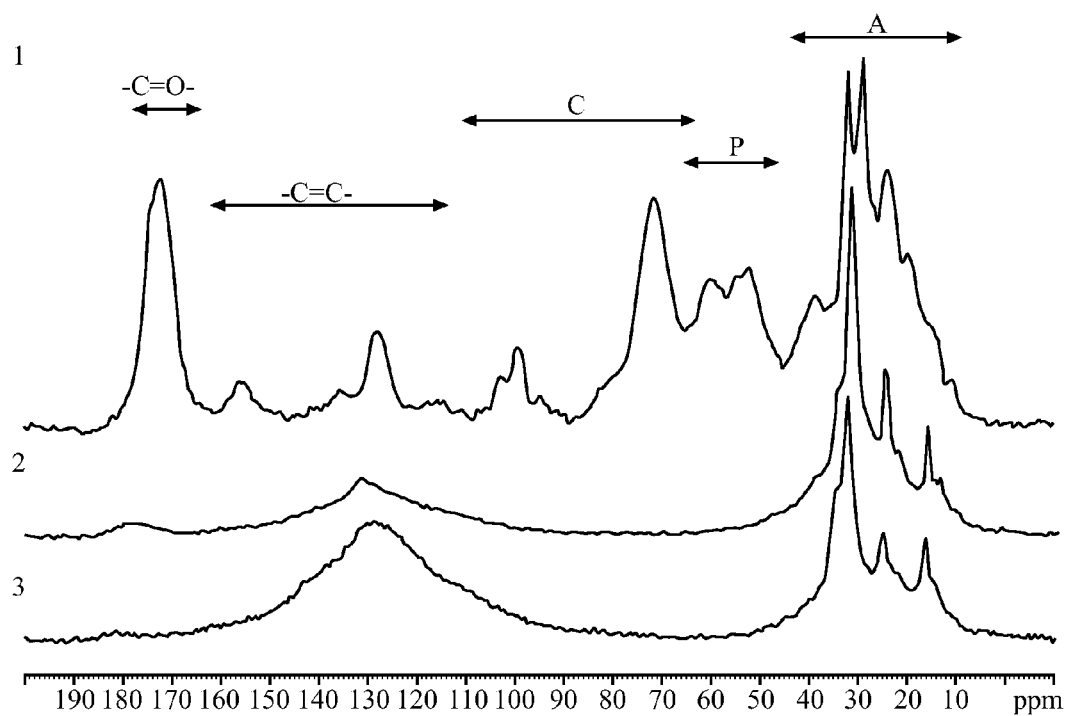
FIG. 4 is $^{13}C$ direct polarization magic angle spinning nuclear magnetic resonance (DPMAS NMR) spectra of (1) freeze dried algae; (2) remaining residue after 260° C. for 72 h water treatment; (3) remaining residue after 360° C. for 72 h water treatment. Region (A) is for aliphatic carbons; (P) is for protein characteristic carbon; (C) is for carbohydrate characteristic carbons.
Figure 5A:
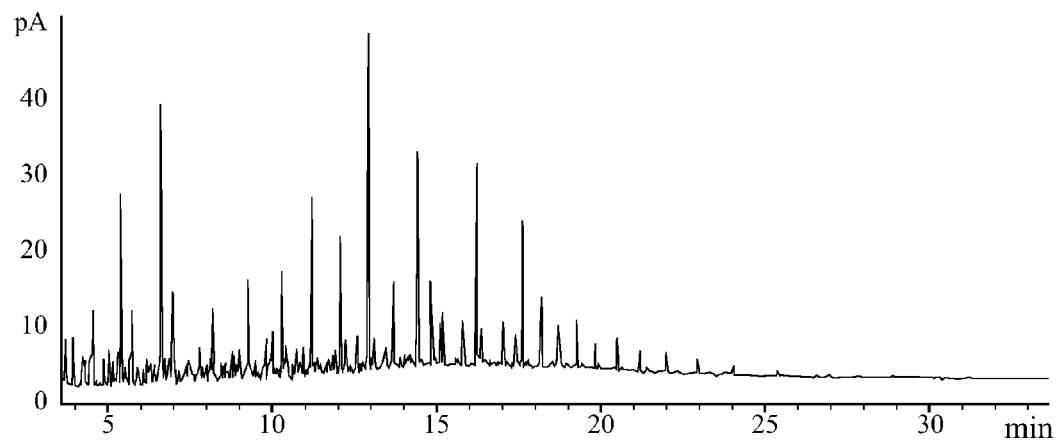
FIG. 5A is a gas chromatogram of the oil floating on the surface of water after pyrolysis experiments on algae at 360° C. for 72 h.
Figure 5B:
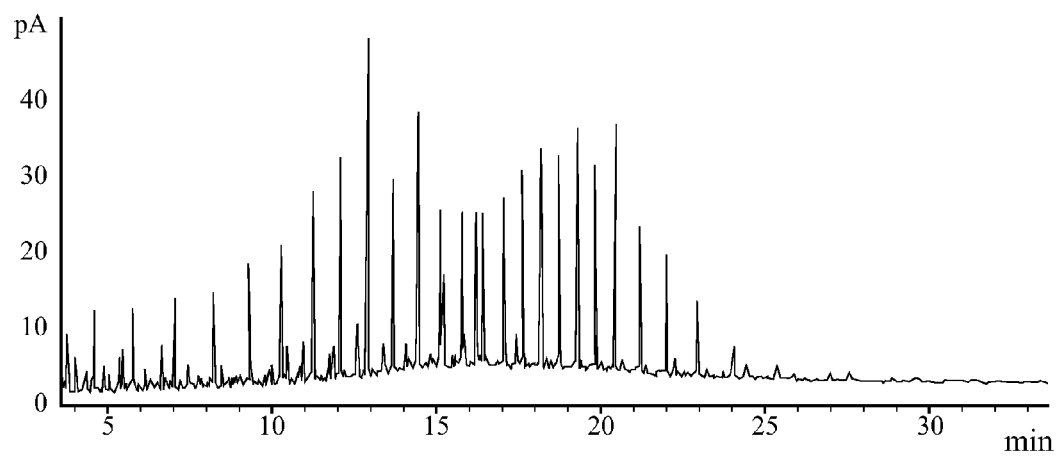
FIG. 5B is a gas chromatogram of the oil floating on the surface of water after pyrolysis experiments on algaenan at 360° C. for 72 h.

Both algaenan and whole algae were subjected to hydrous pyrolysis at 3 temperatures in high-pressure autoclaves. After 72 hours of treatment, the samples were cooled to room temperature. Four different products were collected: 1) gas, 2) hydrocarbon oil floating on the surface of the water, 3) the water, and 4) the remaining solid residue. Each of these isolates was analyzed for their chemical composition. $^{13}$C NMR spectra were collected for whole algae before and after subcritical temperature treatment (FIG. 4). At 260° C. for 72 hours there is a complete disappearance of peaks corresponding to proteins and carbohydrates (peaks at 50, 65, 72, 105, and 175 ppm). These results indicate that carbohydrates and proteins are rendered soluble as they are removed from the solid phase. The main peak remaining in the residue is that of aliphatic algaenan (33, 25, 15 ppm) and a broad peak for aromatic carbons (100-160 ppm). At this temperature, the oil produced is small (8.5% of dry starting mass). At 360° C. for 72 hours the percentage of oil increases significantly to 16.7%. The residue at this temperature shows an increasing amount of aromatic (100-160 ppm) character and the aliphatic algaenan signals diminish in comparison. These results all indicate the following:

1. that carbohydrate and protein separation from algaenan occurs at low temperature, for example, lower than 260° C.
2. that cracking of the algaenan occurs at 360° C.
3. that a significant amount of oil is produced at the higher temperature Analysis of the oil produced at 360° C. for 72 hours from algae by gas chromatography and gas chromatography/mass spectrometry (FIG. 5A, top), shows that the major components are saturated normal hydrocarbons, similar to those observed in some crude oils. The oil obtained from hydrous pyrolysis of the algaenan is similar in composition (FIG. 5B, bottom); its yield at this temperature is 14.5% of the algaenan dry weight. This indicates that the oil produced during hydrous pyrolysis of the whole algae is primarily sourced from the algaenan. The presence of some additional peaks in the oil from whole algae, compared with that from algaenan, is most likely attributable to either lipid triglycerides or presently unknown components of the whole algae. Some of these peaks are alkylated aromatic hydrocarbons, most likely derived from hydrous pyrolysis of proteins.

The algal components, mainly carbohydrates and proteins that are not used for fuel production, dissolve in the aqueous phase. This liquid product can be used as a promising slow-release fertilizer and soil additive, which bestows greater water and inorganic nutrient retention and biomass/crop-supporting capacity. This material provides a high-value co-product that offsets the cost of converting the algae to fuels. Algae can also be cultivated in a manner that removes nitrogen and phosphorus from water and consumes atmospheric $CO_2$; thus, qualifying any fuel produced from this source as renewable energy.

The production of a hydrocarbon-based crude oil from algae will enable a domestic, commercial, alternative, carbon-neutral feedstock for existing refineries. The methods disclosed herein provide a high-value fuel precursor product from algae that supplements the conventional methyl ester biofuel product being exploited commercially and enhances the yield of biofuels from this biomass source. The methods also provide a feedstock that can be readily and directly converted by pyrolytic approaches to a refinable hydrocarbon fuel.

While the invention has been described in connection with certain embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A process for producing selective hydrocarbons from algae comprising:
    providing a feed material of water saturated algae comprising algaenan;
    thermally cracking the algaenan into petroleum-like hydrocarbons by subjecting the water saturated algae to water at a subcritical temperature between 360° C. and less than 374° C., for at least 72 hours, for a in a reactor;
    collecting a liquid phase from the reactor; and
    separating the liquid phase into the petroleum-like hydrocarbons and an aqueous phase product.

2. The process of claim 1, wherein the petroleum-like hydrocarbons have hydrocarbon chain lengths from $C_{10}$ and greater, the hydrocarbon chain lengths being a function of a structure of the algaenan in the water saturated algae provided, wherein different algae comprise different algaenan structure.

3. The process of claim 1, wherein the aqueous phase product is an organic fertilizer.

4. The process of claim 1, further comprising genetically modifying the algaenan prior to providing the water saturated algae as the feed material to produce petroleum-like hydrocarbons with smaller hydrocarbon chain lengths.

5. The process of claim 1, wherein the petroleum-like hydrocarbons are kerosene-like hydrocarbons having hydrocarbon chain lengths from $C_{10}$ to $C_{15}$.

6. The process of claim 1, wherein the petroleum-like hydrocarbons are diesel-like hydrocarbons having hydrocarbon chain lengths from $C_{16}$ to $C_{18}$.

7. The process of claim 1, wherein the petroleum-like hydrocarbons are paraffins having hydrocarbon chain lengths from $C_{18}$ to $C_{32}$.

8. The process of claim 1, wherein the predetermined period of time is approximately 72 hours.

9. The process of claim 1 further comprising chemically modifying the algaenan prior to providing the water saturated algae as the feed material to produce petroleum-like hydrocarbons with smaller hydrocarbon chain lengths.

10. The process of claim 9, wherein chemically modifying the algaenan comprises treating the algaenan with sodium hydroxide to form sodiated fatty acids.

11. The process of claim 9, wherein chemically modifying the algaenan comprises oxidative polymerization of the algaenan.

12. A process for producing selective hydrocarbons from algae comprising:
    extracting algaenan from algae;
    thermally cracking the algaenan into petroleum-like hydrocarbons by subjecting the water saturated algae to water at a subcritical temperature between 360° C. and less than 374° C., for at least 72 hours, in a reactor;
    collecting a liquid phase from the reactor; and
    separating the liquid phase into the petroleum-like hydrocarbons and an aqueous phase product.

13. The process of claim 12, wherein the petroleum-like hydrocarbons have hydrocarbon chain lengths of $C_{10}$ and greater, the hydrocarbon chain lengths being a function of a structure of the algaenan, which is dependent on a type of algae from which the algaenan is extracted.

14. The process of claim 12, further comprising chemically modifying the algaenan to have selective precursors subsequent to extracting the algaenan.

15. The process of claim 14, wherein chemically modifying the algaenan comprises oxidative polymerization of the algaenan.

16. The process of claim 12, wherein aqueous product is an organic fertilizer.

17. A process for producing hydrocarbons and organic fertilizer from one feed material comprising:
   providing a feed material of water saturated algae comprising algaenan;
   thermally cracking algaenan into petroleum-like hydrocarbons by subjecting the water saturated algae having algaenan to water at a subcritical temperature between 360° C. and less than 374° C., in a reactor;
   collecting a liquid phase from the reactor; and
   separating the liquid phase into the petroleum-like hydrocarbons and an aqueous phase product;
   refining the petroleum-like hydrocarbons into one or more of kerosene, diesel, jet fuel, and gasoline; and
   using the aqueous liquid phase product as organic fertilizer.

18. The process of claim 17, further comprising chemically or genetically modifying the algaenan to have selective precursors that function to produce particular hydrocarbon chain lengths.

\* \* \* \* \*